United States Patent
Olah et al.

(10) Patent No.: US 8,461,215 B2
(45) Date of Patent: *Jun. 11, 2013

(54) RENDERING COAL AS AN ENVIRONMENTALLY CARBON DIOXIDE NEUTRAL FUEL AND A REGENERATIVE CARBON SOURCE

(75) Inventors: George A. Olah, Beverly Hills, CA (US); G. K. Surya Prakash, Hacienda Heights, CA (US)

(73) Assignee: University of Southern California, Los Angeles, CA (US)

( * ) Notice: Subject to any disclaimer, the term of this patent is extended or adjusted under 35 U.S.C. 154(b) by 543 days.

This patent is subject to a terminal disclaimer.

(21) Appl. No.: 12/755,934

(22) Filed: Apr. 7, 2010

(65) Prior Publication Data

US 2010/0261125 A1 Oct. 14, 2010

Related U.S. Application Data

(60) Provisional application No. 61/168,297, filed on Apr. 10, 2009.

(51) Int. Cl.
*C07C 27/00* (2006.01)

(52) U.S. Cl.
USPC .............................. 518/700; 518/703; 518/704

(58) Field of Classification Search
USPC .......................................... 518/700, 703, 704
See application file for complete search history.

(56) References Cited

U.S. PATENT DOCUMENTS

| 7,378,561 | B2 | 5/2008 | Olah et al. | 568/885 |
| 2006/0235088 | A1 | 10/2006 | Olah et al. | 518/702 |
| 2006/0287405 | A1 | 12/2006 | Baek et al. | 518/718 |
| 2007/0244208 | A1 * | 10/2007 | Shulenberger et al. | 518/726 |
| 2007/0254969 | A1 | 11/2007 | Olah et al. | 518/726 |
| 2008/0293976 | A1 | 11/2008 | Olah et al. | 568/698 |

FOREIGN PATENT DOCUMENTS

| WO | WO 2008/021700 A1 | 2/2008 |
| WO | WO 2008/157673 A1 | 12/2008 |
| WO | WO 2008/157682 A1 | 12/2008 |

OTHER PUBLICATIONS

International Search Report and Written Opinion of the International Searching Authority, application No. PCT/US2010/030229, Sep. 14, 2010.

* cited by examiner

*Primary Examiner* — Jafar Parsa
(74) *Attorney, Agent, or Firm* — Winston & Strawn LLP

(57) ABSTRACT

The invention provides a method for rendering coal as an environmentally essentially carbon dioxide-neutral fuel. Carbon dioxide produced from coal combustion is captured, purified, combined with coalbed methane or any other natural methane or natural gas source, or with hydrogen, and reacted under reaction conditions sufficient to form methanol and/or dimethyl ether, which can be used as fuel or feedstock for derived synthetic hydrocarbons and products.

22 Claims, No Drawings

RENDERING COAL AS AN ENVIRONMENTALLY CARBON DIOXIDE NEUTRAL FUEL AND A REGENERATIVE CARBON SOURCE

CROSS REFERENCE TO RELATED APPLICATIONS

This application claims the benefit of U.S. application No. 61/168,297 filed Apr. 10, 2009, the entire content of which is incorporated herein by reference thereto.

BACKGROUND

Energy and fuels are essential in modern life. Most widely used type of fuels are fossil fuels. Fossil fuels, including coal, are essentially hydrocarbons containing carbon and hydrogen in various ratios.

Coal, like any carbon-containing fuel, forms carbon dioxide upon its combustion, and therefore is not renewable on the human timescale. Also, because carbon dioxide is a greenhouse gas, combustion of coal contributes to global warming. Although clean coal technology has been developed as a solution to continued use of coal resources, it is so far directed only at reducing harmful pollutants such as sulfur oxides, nitrogen oxides and heavy metals formed from burning coal and does not address carbon dioxide emission. It has been suggested to mitigate harmful carbon dioxide emissions by imposing carbon quota or by capturing carbon dioxide emissions and sequestering it underground or at the bottom of the sea. Sequestration, however, is a costly and only a temporary solution that presents a risk that sequestered carbon dioxide may be released abruptly with deadly catastrophic consequences in the event of geological events such as earthquakes and slides.

Thus, it would be desirable to make coal use environment-friendly and at the same time regenerative by capturing and chemically recycling carbon dioxide emissions to useful fuels and derived products.

SUMMARY OF THE INVENTION

The present invention provides a method for rendering coal as an essentially environmentally carbon dioxide-neutral fuel and regenerative carbon source for producing methanol or dimethyl ether, by capturing and chemically recycling carbon dioxide formed upon coal combustion.

In an embodiment, the method comprises: subjecting coal to reaction conditions sufficient to produce carbon dioxide; capturing and purifying the produced carbon dioxide; combining the carbon dioxide with water and a suitable hydrocarbon source, preferably methane or natural gas, or directly with hydrogen under reaction conditions sufficient to produce methanol or dimethyl ether, so that the carbon dioxide produced from the coal is not emitted to the atmosphere, thus rendering coal as a carbon dioxide-neutral fuel and regenerative carbon source.

The method can further comprise recycling the methanol so produced from carbon dioxide for use as a fuel or feedstock; subjecting the produced methanol fuel or products to reaction conditions to generate carbon dioxide; and repeating the capturing, combining, recycling and subjecting steps on the generated carbon dioxide so that the carbon dioxide produced from the methanol fuel or products made from the methanol feedstock also is not emitted into the atmosphere.

In an example, the carbon dioxide, methane, and water are combined in a molar ratio of about 3:2:1 and are reacted in separate steps or in a single step to produce methanol.

In an embodiment, carbon dioxide is electrochemically reduced to formic acid and related intermediates, which subsequently can be converted to methanol through methyl formate intermediate, as disclosed in U.S. Pat. Application Publication Nos. 2006/0235088 and 2007/0254969.

In another embodiment, the method comprises: combusting coal to produce carbon dioxide; capturing the produced carbon dioxide on an adsorbent; and treating the adsorbent to release the captured carbon dioxide therefrom for use in producing methanol or dimethyl ether. The adsorbent is treated with, for example, sufficient heating, reduced pressure, vacuum, gas purge, or a combination thereof to release the captured carbon dioxide. The adsorbent can be any known material suitable for capturing carbon dioxide. Preferably, the adsorbent comprises a polyamino-containing polymer, such as polyethyleneimine, deposited on a nano-structured support having a high surface area, e.g., nano-structured fused silica or alumina described in U.S. Pat. Application Publication No. 2008/0293976.

In an embodiment, the method further comprises reacting the carbon dioxide with a suitable hydrocarbon source preferably methane or coalbed methane and steam under steam reforming reaction conditions sufficient to form a mixture of hydrogen and carbon monoxide and reacting the carbon dioxide with methane or coalbed methane under dry reforming reaction conditions sufficient to form another mixture of hydrogen and carbon monoxide. The hydrogen and carbon monoxide produced in the steam and dry reforming are then combined for an overall bi-reforming process to form a mixture of hydrogen and carbon monoxide in a molar ratio of about 2 moles of hydrogen to 1 mole of carbon monoxide for reaction to form methanol or dimethyl ether. The molar ratio of hydrogen to carbon monoxide mixture is at least 2:1, and preferably between 2:1 and 2.1:1.

The steam reforming and the dry reforming can be performed simultaneously in a single bireforming step. In an example, bireforming is performed over a catalyst at a temperature between about 800° C. and 1100° C. Suitable catalysts include a single metal catalyst, a single metal oxide catalyst, a mixed catalyst of a metal and a metal oxide, or a mixed catalyst of at least one metal oxide and another metal oxide. The catalyst can be provided on an oxide support. In an example, the catalyst comprises V, Ti, Ga, Mg, Cu, Ni, Mo, Bi, Fe, Mn, Co, Nb, Zr, La or Sn, or an oxide thereof. For example, the catalyst can be NiO or a mixed catalyst of NiO, $V_2O_5$:$Ni_2O_3$, $Ni_2V_2O_7$ and $Ni_3V_2O_5$. The catalyst can be provided on a support of a high surface area nano-structured fumed alumina or fumed silica. In an example, the catalyst is NiO supported on fumed alumina or NiO/$V_2O_5$ supported on fumed silica.

Suitable hydrocarbon sources used in the present processes, which preferably are methane or natural gas, can be obtained from any available source, including coalbed methane accompanying coal mining or any other natural hydrocarbon source.

Hydrogen needed for the chemical recycling carbon dioxide according to the present processes can also be directly generated from water, e.g., by electrolysis or any other means of cleavage, or by photochemical or thermal decomposition, using any energy source, including electricity generated by coal-burning power plants, e.g., during off-peak periods, or any alternate energy source (e.g., solar, wind, hydro or atomic energy).

In an example, methanol produced according to the invention is dehydrated by removing water under conditions sufficient to produce dimethyl ether, and the removed water is recycled during reforming, such as in the bi-reforming process.

The methanol produced according to the present process can be used as is or can be converted to dimethyl ether. Methanol and dimethyl ether can be used as fuels or chemical feedstocks for the production of various derived products.

Methanol and dimethyl ether produced according to the present processes can be reacted in the presence of an acidic-basic or zeolitic catalyst under conditions sufficient to form ethylene or propylene. Ethylene or propylene can in turn be converted to produce synthetic hydrocarbons, chemicals, polymers, or various products derived therefrom.

The produced methanol can be combusted in a power plant to produce energy and generate carbon dioxide with the generated carbon dioxide recycled to the other process steps for producing methanol. This avoids release of the carbon dioxide into the atmosphere and avoids having to otherwise handle or sequester carbon dioxide.

The methods of the invention can be carried out while co-generating electricity or energy from coal combustion. For example, the method can be carried out in an electricity-producing coal-burning power plant. Methanol produced according to the present method can be combusted, optionally in a mixture that includes gasoline, in a power plant that produces energy with the combusted methanol. Carbon dioxide generated from combusting methanol is recycled for producing methanol. Similarly, dimethyl ether produced according to the present method can be used as a diesel fuel substitute, as optionally in a mixture that includes natural gas, in a power plant that produces energy while also generating carbon dioxide. The carbon dioxide so generated is recycled for producing methanol and dimethyl ether.

Thus, the present processes advantageously provide the recycling of carbon dioxide from coal combustion for the production of methanol, dimethyl ether, and their derived products in an integrated, efficient and economical industrial operation that is environmentally beneficial by not releasing the carbon dioxide to the atmosphere.

DESCRIPTION OF THE PREFERRED EMBODIMENTS

The invention relates to processes for the capture, isolation and purification of carbon dioxide from coal combustion and its chemical recycling to methanol and dimethyl ether.

A preferred embodiment of the invention relates to a method for rendering coal as an essentially environmentally carbon dioxide-neutral fuel and regenerative carbon source, by subjecting coal to reaction conditions sufficient to produce carbon dioxide; capturing and purifying the produced carbon dioxide; and combining the purified carbon dioxide with water and a suitable hydrocarbon source or with hydrogen under reaction conditions sufficient to produce methanol or dimethyl ether, so that the carbon dioxide generated from the coal is not introduced into the atmosphere, thus rendering the coal as an essentially environmentally carbon dioxide-neutral fuel.

Also, by chemically recycling carbon dioxide formed from coal use to produce methanol and/or dimethyl ether, the invention advantageously renders coal a regenerative carbon source for producing methanol, dimethyl ether and derived products. And if the methanol or dimethyl ether is combusted to generate carbon dioxide and the carbon dioxide is subsequently recovered and recycled for making more methanol or dimethyl ether, those compounds will also become environmentally neutral with the carbon dioxide not being released into the atmosphere and instead being continuously recycled.

The invention thus advantageously renders coal as an essentially environmentally carbon dioxide-neutral fuel. As used herein, "environmentally carbon dioxide-neutral fuel" means that the fuel is used in such a way that its use does not release or introduce carbon dioxide into the environment, i.e., carbon dioxide is not released into the atmosphere nor sequestered. Thus, the present processes of rendering coal an essentially environmentally carbon dioxide-neutral fuel reduce the carbon footprint of using natural gas and are environmentally beneficial. As used herein, "essentially environmentally carbon dioxide-neutral fuel" and "substantially environmentally carbon dioxide-neutral fuel" mean that coal is used in such a way that its use does not release or introduce carbon dioxide into the environment except in minor amounts, e.g., less than 10%, preferably less than 5%, and more preferably less then 3%, of the total carbon dioxide produced from using the fuel.

In an embodiment, carbon dioxide is captured following coal combustion, purified and chemically recycled by reaction into methanol, which can be used as a fuel or chemical feedstock. Methanol can be converted to dimethyl ether, which can be utilized as a fuel for transportation or as household gas for heating and cooking. Methanol and dimethyl ether can be converted into ethylene or propylene, which can be used as building blocks of synthetic hydrocarbons, chemicals, and polymers, which in turn can be used to produce various products.

According to the processes of the invention, carbon dioxide is chemically recycled instead of being released to the atmosphere or being sequestered, thus avoiding or mitigating carbon dioxide release into the environment that results from coal combustion while providing a regenerative carbon source for producing fuels and products. The present processes thus permanently and economically avoid or mitigate the release of carbon dioxide into the environment and is environmentally beneficial. Thus, the processes renders coal an essentially environmentally carbon dioxide-neutral fuel and also a regenerative carbon source.

The present processes can be used with any method of coal combustion or any method of generating energy from coal that produces carbon dioxide. For example, the processes can be used with coal combustion in power plants and industrial plants. In further embodiments, methanol produced according to the present processes can be combusted, optionally in a mixture that includes gasoline, in a power plant that produces energy with the combusted methanol, thus also generating carbon dioxide. The generated carbon dioxide can be recycled to produce methanol. Similarly, dimethyl ether produced according to the present processes can be combusted, optionally in a mixture that includes natural gas, in a power plant that produces energy from the combustion, thus also generating carbon dioxide. The generated carbon dioxide can be recycled to produce methanol, which in turn can be used to produce additional dimethyl ether.

Carbon dioxide is captured, isolated and purified using any suitable, known methods, such as by membrane separation or with a suitable absorbing device or material. A suitable process for capturing and reversibly adsorbing carbon dioxide from a gas mixture by using a nano-structured supported absorbent such as fumed silica is disclosed in U.S. Pat. No. 7,378,561, the entire content of which is incorporated herein by reference. Captured carbon dioxide can be readily released through, for example, heating, reduced pressure, vacuum, gas purge, or a combination thereof, for use in the reactions described herein. Prior to its utilization, carbon dioxide is purified by any suitable, known method, e.g., by absorbing pollutants and contaminants therein. The captured and/or purified carbon dioxide is then recycled and converted to methanol or dimethyl ether.

If methane is available from, for example, coalbed methane accompanying coal mining operations, or from any other natural or industrial source, carbon dioxide is preferably converted to methanol and/or dimethyl ether using a process of conversion that is referred to as bi-reforming (described in U.S. Pat. Application Publication No. 2008/0319093) and that utilizes a specific combination of steam ($H_2O$) reforming and dry ($CO_2$) reforming of methane, performed in two steps or combined into a single step. The method comprises reacting methane under a combination of conditions of steam (wet) and dry ($CO_2$) reforming in a specific molar ratio of reactants sufficient to produce a mixture of hydrogen and carbon monoxide ($H_2$/CO) in a molar ratio of about 2:1, which is sufficient to convert such mixture of $H_2$ and CO exclusively to methanol or dimethyl ether. In a preferred embodiment, the molar ration of hydrogen and carbon monoxide is between 2:1 and 2.1:1. Advantageously, the mixture of reactants is treated without separation of its components to convert substantially all the reactants to methyl alcohol or dimethyl ether without producing byproducts. Any unreacted starting or intermediate products can be readily recovered and recycled.

The steps of the process of the invention for the production of methanol are illustrated by the following reactions:

Step A

Steam reforming

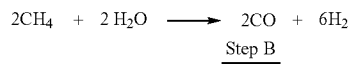

Step B

Dry reforming

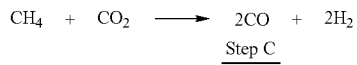

Step C

Bireforming

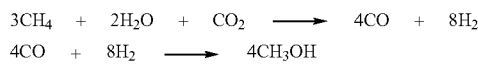

The process of producing methanol can be practiced by carrying out the reforming steps separately. The products of reforming of steps A and B are mixed to provide close 2:1 ratio of $H_2$ and CO before being introduced into the methanol producing step. The two reforming steps also can be combined into a single bireforming step C. In that case, methane, steam (water) and carbon dioxide are reacted preferably in the molar ratio of about 3:2:1 to form a mixture of 2 moles of hydrogen and 1 mole of carbon dioxide.

This process completely converts carbon dioxide to methanol without producing any byproduct, such that essentially no carbon dioxide is released into the atmosphere or needs to be sequestered. This provides significant economical and environmental advantages. For example, in contrast to the known tri-reforming process of methane, in which a combination of dry reforming, steam reforming and partial oxidation of methane is carried out in a single step but which produces $CO_2$ as a significant excess byproduct in the oxidation step, the present process provides improved control, high selectivity, and high yield of the conversion of carbon dioxide to methanol, without producing any byproducts and the disadvantages associated with concurrent partial oxidation that results in undesirable excess carbon dioxide.

When producing dimethyl ether, water obtained from the dehydration of methanol can be recycled in the bi-reforming of carbon dioxide and methane, such that no byproduct water is wasted in the overall process. This is particularly advantageous in arid areas or places where pure water is not readily available.

The steps of the present process are illustrated below:

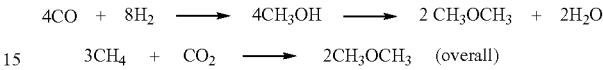

Dehydration of the methanol can be effected over a suitable silica, alumina, or other solid acidic catalyst, including polymeric acid catalysts such as Nafion-H, at a temperature sufficient for the removal of the water. Operative temperature are in the range of 100° C. to 200° C.

It will be appreciated that the present reforming processes can be used with any suitable hydrocarbon source in addition to methane. Suitable hydrocarbon sources, as used herein, include methane, natural gas and light hydrocarbon fractions of petroleum oil.

Thus, in an embodiment, bi-reforming for the recycling of $CO_2$ according to the invention can be applied directly to light hydrocarbon fractions to produce methanol or dimethyl ether in a separate step or in a single step with a proper ratio of mixing to obtain a $H_2$ and CO molar mixture of at least 2 moles of hydrogen to 1 mole of carbon monoxide required for the production of methanol.

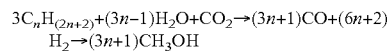

The bi-reforming process for recycling of $CO_2$ produces a $H_2$/CO mixture with a molar ratio of at least 2 to 1 required for methanol synthesis. It utilizes a specific combination of steam and dry reforming of methane with $CO_2$. In the subsequent methanol synthesis step, substantially all of the hydrogen is converted to methanol. As described in U.S. Pat. Application Publication Nos. 2006/0235088 and 2007/0254969, this subsequent step can be performed, without limitation, by direct catalytic conversion, or by a reaction that involves a methyl formate intermediate.

In a preferred embodiment of this invention, a specific combination of steam and dry reforming of methane is used to achieve a molar ratio of $H_2$ and CO close to at least 2 moles hydrogen to 1 mole of carbon monoxide for the conversion to methanol. The conversion temperature is in the range from about 800° C. to about 1100° C., preferably about 850° C. to about 950° C. A catalyst or a combination of catalysts can be used. Suitable catalysts include alkali oxides, alkaline oxides or metal oxides, such as V, Ti, Ga, Mg, Cu, Mo, Bi, Fe, Mn, Co, Nb, Zr, La or Sn. Catalysts can be used alone in combination, and can be supported on a suitable high surface area support such as silica or alumina. Exemplary single or metal oxide combinations include NiO, NiO:$V_2O_5$, $V_2O_5$:$Ni_2O_3$, metal-metal oxides such as $N_1$—$V_2O_5$, ($M_2O_3$—$V_2O_5$), and mixed oxides such as $Ni_2V_2O_7$, $Ni_3V_2O_5$ and $Ni_3V_2O_8$. In a preferred embodiment, the catalyst is NiO supported on fumed alumina or NiO/$V_2O_5$ supported on fumed silica. It will be appreciated that a number of other related metal and metal oxide catalysts, and their combinations, can be used.

Suitable reactors for the conversion reactions can be used. For example, a continuous flow reactor under appropriate reaction conditions can be used.

The energy required for the present processes for chemically recycling carbon dioxide can be provided from any suitable source. For example, when practicing the process in a power plant, the energy produced by the power plant itself can be used. In other examples, any alternative energy (solar, wind, water (hydro), etc.) or atomic energy sources can be used. The present recycling process of carbon dioxide from coal combustion to produce methanol and/or dimethyl ether is an energy storage and fuel production process that can use any available energy to produce useful products and eliminate carbon dioxide emissions.

Any hydrocarbon source can be used in the present processes. Where desired, for example, in the absence of a convenient and economical hydrocarbon source, the processes can directly utilize hydrogen. Hydrogen obtained by known methods of electrolysis or cleavage of water can also be used. Energy for this purpose can be provided from any of the previously mentioned energy sources or by photolytic, thermal or enzymatic ways. The utilization of water as the needed hydrogen source for the conversion of recycled carbon dioxide is described in U.S. Patent Application Publication No. 2007/0254969.

In an embodiment, efficient and economical aqueous electrochemical conversion of $CO_2$ to methanol is provided. $CO_2$ can be electrochemically reduced with good selectivity to formic acid, as described in U.S. Pat. Application Publication No. 2007/0254969:

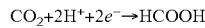

$$CO_2 + 2H^+ + 2e^- \rightarrow HCOOH$$

Formic acid is then recombined with methanol (to be recycled from the process) to form methyl formate, which is subsequently hydrogenated to form exclusively two moles of methanol under relatively mild conditions:

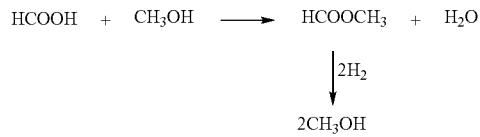

This embodiment allows significant energy savings, since hydrogen is used only in producing methanol, and the needed hydrogen can come from formic acid itself.

Advantageously, the present processes achieve substantially complete recycling of carbon dioxide to produce methanol and/or dimethyl ether, thus providing an efficient and economical way of rendering coal a regenerative, environmentally carbon dioxide-neutral fuel and chemical source.

In the present processes, carbon dioxide formed in coal combustion is captured and chemically recycled to methanol and/or dimethyl ether. This makes possible efficient and economical cogeneration of electricity and production of methanol and dimethyl ether (as well as various products derived therefrom) in an integrated industrial cycle of substantial utility and value. The present processes also allow efficient load management of coal-burning power plants during off-peak periods.

Methanol and dimethyl ether produced according to the invention can be used in numerous applications, either by themselves or upon subsequent conversion to other products. For example, methanol, dimethyl ether and their derived products can be used as synthetic internal combustion (ICE) fuels, gasoline-methanol mixed fuels (prepared by adding methanol to gasoline with the fuel having a minimum gasoline content of at least 15% by volume), diesel fuels, or as fuels for fuel cells. Methanol and dimethyl ether also are convenient energy storage and transportation materials that minimize or eliminate the disadvantages and dangers inherent in the use and transportation of LNG or LPG. Dimethyl ether is also a convenient household gas that can replace natural gas or can be mixed with natural gas or liquefied petroleum gas.

Methanol and dimethyl ether also are convenient raw materials for producing olefins, derived hydrocarbon products and polymers. Various products that can be made with methanol, dimethyl ether, or other methanol-derived chemicals are well known and include basic chemicals such as formaldehyde, acetic acid, methyl-tert-butyl ether (MTBE); olefins such as ethylene and propylene, which in turn can be used to form ethanol and propanol, higher olefins, polyolefins, synthetic hydrocarbons, and aromatic compounds; various other polymers; and chemicals such as chloromethanes, methylamines, methyl methacrylate, and dimethyl terephthalate, which can be further processed to manufacture products such as paints, resins, silicones, adhesives, antifreeze, plastics, and construction materials. These and other uses of methanol, dimethyl ether, and their derivative products are well known and will be appreciated by ordinary-skilled artisans. These products retain the carbon rather than releasing it into the atmosphere. At the end of the useful life of these materials, and in particular for polymers, they can be recycled and made into new polymeric products. Furthermore, materials that are not usable for recycling can be combusted with the carbon dioxide recovered as discussed above and then recycled to make methanol.

Another use for methanol is as a source for preparing single-cell proteins for human or animal consumption. Again, the carbon dioxide that is recovered and made into methanol is put to use rather than being emitted as an off-gas.

The invention can permanently avoid or mitigate the release of the carbon dioxide upon combustion of coal into the environment. This collection and recycling of the generated carbon dioxide avoids its release into the atmosphere, or avoids the need for sequestration underground or in the sea. Instead, methanol is made, combusted, and made again so that the carbon dioxide becomes an important reactant in a renewable fuel cycle.

The invention is not to be limited in scope to the specific embodiments herein disclosed, as these embodiments are intended as illustrative of aspects of the invention. Any equivalent embodiments will become apparent to those of ordinary skill in the art and are intended to be included within the scope of the invention.

EXAMPLES

The following examples are provided for purposes of illustrating preferred embodiments of the invention and are not limiting.

Example 1

Coal is combusted (with air or pure oxygen) in a power plant and the flue gas that is generated is directed to a capture and purification process rather than being emitted to the atmosphere. Carbon dioxide is removed by being adsorbed or by passing through any suitable adsorbing system containing an adsorbent that is known to efficiently adsorb carbon dioxide. An efficient but not limiting adsorbent system for removing carbon dioxide can include a polyethyleneimine polymer or other polyamino-group containing polymers supported on fumed silica, alumina or other suitable support of nano-structured nature with a high surface area or activity, according to U.S. Pat. Application Publication No. 2008/0293976. Carbon dioxide is subsequently desorbed by heating or applying reduced pressure, and is then converted chemically to methanol. Carbon dioxide thus obtained can then be used as a reactant in the processes disclosed herein.

Example 2

Carbon dioxide is captured and purified from the exhausts of natural gas burning electric power plants or any other industrial plants according to Example 1 by any known and suitable method including absorption by nano-structured fumed silica, alumina as disclosed. It is then subsequently converted to methanol or dimethyl ether according to the processes disclosed herein, instead of being sequestered.

Example 3

A suitable molar mixture of $CO_2$, methane (from coalbed methane or other natural sources), and steam is bi-reformed, allowing for a conversion of $CO_2$ in excess of 90% in a flow reactor over a catalyst such as $V_2O_5/NiO$ at a temperature of about 800° C. to 850° C. to produce a gas mixture with a molar ratio of approximately 2.05 moles of hydrogen to 1 mole of carbon monoxide. The catalyst support is preferably fused silica (or alumina) having suitably large nano-structured surfaces.

Example 4

Hydrogen and carbon monoxide produced as in Example 3 are subsequently converted to produce methanol under catalytic reaction conditions using copper based catalysts.

Example 5

The methanol produced in Example 4 is dehydrated using a solid acidic catalyst such as silica, alumina or synthetic polymeric sulfonic acids such as Nafion-H to produce dimethyl ether.

Example 6

The water produced in the process of producing dimethyl ether in Example 5 is recycled to allow for the continuous conversion of $CO_2$ with methane (natural gas) to produce dimethyl ether, such that water is used in the reaction rather than wasted as a byproduct.

Example 7

The methanol produced in Examples 1 to 4 is conveniently used as a convenient liquid fuel or a suitable flexfuel by mixing with gasoline and optionally with a small amount of ethanol. Methanol can also be used in fuel cells. It can also be used as starting materials for synthetic hydrocarbons and derived products. The fuel can be transported to a power plant or other energy producing facility where it can be combusted in place of coal, oil or natural gas. In this plant, the carbon dioxide that is generated is captured and recovered for recycle to produce further methanol.

Example 8

The dimethyl ether produced in Examples 5 and 6 can be used as a high cetane diesel substitute and can be mixed with natural gas and liquefied petroleum gas for fuel use. The fuel is transported to a power plant or other energy producing facility where it can be combusted in place of coal, oil or natural gas.

What is claimed is:

1. A method for rendering coal as an essentially environmentally carbon dioxide-neutral fuel and regenerative carbon source, which comprises:
   subjecting coal to reaction conditions sufficient to produce carbon dioxide;
   capturing and purifying the produced carbon dioxide; and
   combining the purified carbon dioxide with water and a suitable hydrocarbon source having the formulation of $C_nH_{(2n+2)}$, in a molar ratio of 3:(3n−1):1 as $3C_nH_{(2n+2)} + (3n−1)H_2O + CO_2$ to conduct a bi-reforming reaction by:
   conducting steam reforming of the hydrocarbon with water to form carbon monoxide and hydrogen;
   conducting dry reforming of the hydrocarbon with carbon dioxide to form carbon monoxide and hydrogen;
   combining effluents including carbon monoxide and hydrogen from the steam and dry reforming reactions without separation of components of the reforming reactions or their effluents to produce a mixture of hydrogen and carbon monoxide having a molar ratio of hydrogen to carbon monoxide that is about 2:1 to 2.1:1; and
   converting the molar mixture of hydrogen and carbon monoxide under conditions sufficient to exclusively form methanol, as follows:

$$(3n+1)CO + (6n+2)H_2 \rightarrow (3n+1)CH_3OH,$$

so that the carbon dioxide generated from the coal is not introduced into the atmosphere, thus rendering the coal as an essentially environmentally carbon dioxide-neutral fuel.

2. The method of claim 1 which further comprises:
   recycling the methanol for use as a fuel or feedstock;
   subjecting the methanol fuel or products made from the feedstock to reaction conditions to generate carbon dioxide; and
   repeating the capturing, combining, recycling and subjecting steps on the generated carbon dioxide so that the carbon dioxide produced from the methanol fuel or products made from methanol feedstock also is not emitted to the atmosphere.

3. The method of claim 1, wherein the subjecting step generates energy and is performed in a power plant.

4. The method of claim 1, wherein the carbon dioxide, suitable hydrocarbon source, and water are reacted in separate steps or in a single step to produce methanol.

5. The method of claim 1, wherein the suitable hydrocarbon source is methane or coalbed methane or natural gas.

6. The method of claim 1, which further comprises:
   combusting the coal to produce carbon dioxide;
   capturing the produced carbon dioxide on an adsorbent; and
   treating the adsorbent to release the captured carbon dioxide therefrom for use in producing methanol or dimethyl ether.

7. The method of claim 6, wherein the adsorbent is treated with sufficient heating, reduced pressure, vacuum, gas purge, or a combination thereof to release the captured carbon dioxide.

8. The method of claim 6, wherein the absorbent is a polyamino-containing polymer deposited on a nano-structured supporting having a high surface area.

9. The method of claim 8, wherein the polyamino-containing polymer is polyethyleneimine and the support is nano-structured fused silica or alumina.

10. The method of claim 1, wherein the steam reforming and the dry reforming are performed simultaneously in a single bireforming step.

11. The method of claim 1, wherein the methane, steam and carbon dioxide are reacted in a single step in a molar ratio of about 3:2:1 to form a mixture of hydrogen and carbon dioxide in a molar ratio of about 2:1.

12. The method of claim 1, wherein the steam reforming and the dry reforming are performed simultaneously in a single step over a catalyst at a temperature between about 800° C. and 1100° C.

13. The method of claim 12, wherein the catalyst is provided on a support of a high surface area nano-structured fumed alumina or fumed silica.

14. The method of claim 12, wherein the catalyst comprises V, Ti, Ga, Mg, Cu, Ni, Mo, Bi, Fe, Mn, Co, Nb, Zr, La or Sn, or an oxide thereof.

15. The method of claim 12, wherein the catalyst comprises a single metal catalyst, a single metal oxide catalyst, a mixed catalyst of a metal and a metal oxide, or a mixed catalyst of at least one metal oxide and another metal oxide, the catalyst optionally being provided on an oxide support.

16. The method of claim 15, wherein the catalyst is NiO or a mixed catalyst of NiO, $V_2O_5:Ni_2O_3$, $Ni_2V_2O_7$ and $Ni_3V_2O_5$.

17. The method of claim 15, wherein the catalyst is NiO supported on fumed alumina or $NiO/V_2O_5$ supported on fumed silica.

18. The method of claim 1, which further comprises dehydrating methanol by removing water under conditions sufficient to produce dimethyl ether and recycling the water from dehydration during subsequent reforming.

19. The method of claim 18, which further comprises reacting the dimethyl ether in the presence of an acidic-basic or zeolitic catalyst under conditions sufficient to form ethylene or propylene.

20. The method of claim 19, which further comprises converting ethylene or propylene under conditions sufficient to produce synthetic hydrocarbons, chemicals, or polymers.

21. The method of claim 1, which further comprises combusting the produced methanol, optionally in a mixture that includes gasoline, in a power plant that produces energy with the combusted methanol while also generating carbon dioxide and recycling the generated carbon dioxide for producing methanol.

22. The method of claim 18, which further comprises combusting the produced dimethyl ether, optionally in a mixture that includes natural gas and liquefied petroleum gas, in a power plant that produces energy while also generating carbon dioxide and recycling the generated carbon dioxide for producing methanol which in turn produces additional dimethyl ether.

* * * * *